United States Patent
Mori et al.

(10) Patent No.: US 10,307,495 B2
(45) Date of Patent: Jun. 4, 2019

(54) STERILIZING APPARATUS

(71) Applicant: SHARP KABUSHIKI KAISHA, Sakai, Osaka (JP)

(72) Inventors: Jun Mori, Sakai (JP); Tim Michael Smeeton, Oxford (GB)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

(21) Appl. No.: 15/512,423

(22) PCT Filed: Jun. 29, 2015

(86) PCT No.: PCT/JP2015/068734
§ 371 (c)(1),
(2) Date: Mar. 17, 2017

(87) PCT Pub. No.: WO2016/042879
PCT Pub. Date: Mar. 24, 2016

(65) Prior Publication Data
US 2017/0290932 A1   Oct. 12, 2017

(30) Foreign Application Priority Data
Sep. 19, 2014 (JP) ................. 2014-191511

(51) Int. Cl.
*A61L 2/00* (2006.01)
*A61N 5/06* (2006.01)
*A61N 5/067* (2006.01)

(52) U.S. Cl.
CPC .............. *A61L 2/0047* (2013.01); *A61N 5/06* (2013.01); *A61N 5/0613* (2013.01);
(Continued)

(58) Field of Classification Search
CPC ........ A61L 2/0047; A61L 2/10; A61L 2/0052; A61L 2/084; A61N 5/06; A61N 5/0613;
(Continued)

(56) References Cited

U.S. PATENT DOCUMENTS

| | | |
|---|---|---|
| 5,178,616 A | 1/1993 | Uemiya et al. |
| 5,906,609 A | 5/1999 | Assa et al. |
| 2006/0104859 A1 | 5/2006 | Tribelsky |
| 2010/0291502 A1 | 11/2010 | Knight |

(Continued)

FOREIGN PATENT DOCUMENTS

| | | |
|---|---|---|
| JP | 1-308550 A | 12/1989 |
| JP | 10-146394 A | 6/1998 |

(Continued)

OTHER PUBLICATIONS

Manuela Buonanno et al., "207-nm UV Light—A Promising Tool for Safe Low-Cost Reduction of Surgical Site Infections. I: In Vitro Studies", PLOS One, Oct. 2013, vol. 8, Issue 10, e76988, pp. 1-7.

*Primary Examiner* — Timothy C Cleveland
(74) *Attorney, Agent, or Firm* — Birch, Stewart, Kolasch & Birch, LLP

(57) ABSTRACT

A sterilizing apparatus having both excellent safety and operability is provided. A sterilizing apparatus (1) according to an aspect for carrying out the present invention is a sterilizing apparatus (1) that radiates light including ultraviolet rays onto an affected area (6), wherein first wavelength light ($L_{\lambda 1}$) having a peak wavelength in a wavelength range of 190 nm or more and 230 nm or less, and second wavelength light ($L_{\lambda 2}$) having a peak wavelength in a wavelength range of 400 nm or more and 780 nm or less are emitted.

5 Claims, 5 Drawing Sheets

(52) U.S. Cl.
CPC .......... *A61N 5/0624* (2013.01); *A61N 5/0601* (2013.01); *A61N 2005/063* (2013.01); *A61N 2005/067* (2013.01); *A61N 2005/0643* (2013.01); *A61N 2005/0647* (2013.01); *A61N 2005/0661* (2013.01)

(58) Field of Classification Search
CPC ................. A61N 5/0601; A61N 5/624; A61N 2005/063; A61N 2005/0643; A61N 2005/0647; A61N 2005/0661; A61N 2005/067
See application file for complete search history.

(56) References Cited

U.S. PATENT DOCUMENTS

| | | |
|---|---|---|
| 2011/0054574 A1 | 3/2011 | Felix |
| 2013/0015362 A1 | 1/2013 | Hooper et al. |
| 2013/0100977 A1 | 4/2013 | Smeeton et al. |
| 2014/0251949 A1 | 9/2014 | Smeeton et al. |
| 2015/0073396 A1 | 3/2015 | Randers-Pehrson et al. |
| 2015/0177593 A1 | 6/2015 | Smeeton et al. |

FOREIGN PATENT DOCUMENTS

| | | |
|---|---|---|
| JP | 10-248759 A | 9/1998 |
| JP | 10-328289 A | 12/1998 |
| JP | 2005-111034 A | 4/2005 |
| JP | 2006-502756 A | 1/2006 |
| JP | 2010-264238 A | 11/2010 |
| JP | 2013-66685 A | 4/2013 |
| JP | 2013-88822 A | 5/2013 |
| JP | 2014-508612 A | 4/2014 |
| JP | 2015-112439 A | 6/2015 |

STERILIZING APPARATUS

TECHNICAL FIELD

The present invention relates to a sterilizing apparatus that sterilizes by radiating ultraviolet rays, and more specifically, relates to a sterilizing apparatus capable of visualizing the irradiation range of the ultraviolet rays.

BACKGROUND ART

In the medical practice of "surgery" where the risk of infection is high, there is no method for preventing infections 100%, and surgical site infections (SSIs) occur in 2% to 5%.

In order to reduce surgical site infections (SSIs), it is necessary to pay attention to surgery as a whole, such as complications of the patient, disinfection, the operating theater environment, disinfection/infection management for medical practitioners, and the like. Surgery is usually performed under aseptic conditions, and sufficient consideration is given to hygiene in all situations in medical settings; however, the occurrence rate of surgical site infections (SSIs) differs depending on the type of surgery and the site on which surgery is to be performed. This is due to the degree of difficulty of the process of sterilizing (disinfecting) the site.

For example, in catheter surgery in which a catheter is placed (indwelled) in a blood vessel or ureter, the occurrence rate of surgical site infections (SSIs) exceeds 10% (JANIS, SSI Department, Public Information, July to December 2013 Semiannual Report). The reason for this is because it is not possible to directly sterilize such surgical sites, and because there is currently no method other than to thoroughly sterilize the catheter to be inserted.

Recovery being delayed due to a surgical site infection (SSI) causes an increase in the hospitalization period and medical costs, ultimately resulting in a burden being placed on the patient. Hospitalization periods extend by 15 to 18 days on average, and hospital expenses increase by an average of approximately 450,000 to 540,000 yen per case.

The number of incidences of surgical site infections (SSIs) in Japan is 5,374 cases (JANIS, SSI Department, Public Information, July to December 2013 Semiannual Report), which calculates to additional medical expenses of approximately 4.8 billion yen each year due to the occurrence of surgical site infections (SSIs). Furthermore, the psychological burden on patients faced with the situation of an increased financial burden due to not being able to leave the hospital for a while after surgery cannot be overlooked. Therefore, the development of a technique capable of reducing the occurrence rate of surgical site infections (SSIs) is desired.

Regarding such a technique, PTL 1 discloses a technique for sterilizing a surgical site using an ultraviolet lamp. According to PTL 1, it is possible to sterilize an area including a surgical site by radiating ultraviolet rays using an ultraviolet lamp. Additionally, by radiating visible light rays together with ultraviolet rays, the irradiation range of the ultraviolet rays is visualized.

Furthermore, PTL 2 discloses a sterilizing apparatus provided with: an ultraviolet lamp that emits ultraviolet rays of a wavelength range of approximately 190 nm to 230 nm; and a spectrum filter element such as multilayer dielectric filter or a chemical filter that substantially prevents the inclusion of light outside of the aforementioned wavelength range in the ultraviolet rays. According to PTL 2, it is possible to sterilize microbial bacteria without harming human body cells.

Furthermore, NPL 1 discloses a sterilization technique by means of a Kr—Br excimer lamp of a peak wavelength of 207 nm, in which light of a wavelength of 210 nm or more is removed with a filter. According to NPL 1, it is possible to sterilize microbial bacteria while suppressing harm to human body cells and the occurrence of mutation in skin cells.

Furthermore, PTL 3 describes a method for treating periodontal disease in which ultraviolet rays are guided from an ultraviolet ray light source by means of an optical fiber and radiated onto an affected area. According to PTL 3, it is possible to sterilize periodontal pathogenic bacteria by attaching an optical fiber to the tip end of an instrument or the like used by dentists.

CITATION LIST

Patent Literature

PTL 1: Japanese Unexamined Patent Application Publication No. 10-328289 (published on 15 Dec. 1998)
PTL 2: Japanese Unexamined Patent Application Publication (Translation of PCT Application) No. 2014-508612 (published on 10 Apr. 2014)
PTL 3: Japanese Unexamined Patent Application Publication No. 2013-66685 (published on 18 Apr. 2013)

Non-Patent Literature

NPL 1: Plos ONE8(10)e76968 (published on 15 Oct. 2013)

SUMMARY OF INVENTION

Technical Problem

However, in the aforementioned techniques of the past, there are the following problems. More specifically, in PTL 1, the wavelengths of the ultraviolet rays and visible light rays radiated onto an affected area are not specified, and therefore, depending on the wavelength of the ultraviolet rays that are radiated, there is a problem in that human body cells are harmed.

Furthermore, in PTL 2 and NPL 1, only ultraviolet rays are radiated, and therefore the irradiation range of the ultraviolet rays cannot be visualized. In an actual surgical environment, it is necessary for ultraviolet rays to be quickly radiated onto a target affected area. Therefore, the fact that the irradiation range of the ultraviolet rays cannot be visualized is a problem in that there are handling difficulties in a surgical environment. Moreover, PTL 2 proposes a technique in which a fluorescent material is used as an absorption material to indicate that a lamp is in operation by emitting visible light rays when ultraviolet rays are absorbed; however, this technique does not visualize the irradiation range of the ultraviolet rays.

Furthermore, in PTL 3, the wavelength of the ultraviolet rays radiated onto an affected area are not specified, and therefore, depending on the wavelength of the ultraviolet rays that are radiated, there is a problem in that human body cells are harmed. Furthermore, in PTL 3, only ultraviolet rays are radiated, and therefore the irradiation range of the ultraviolet rays cannot be visualized.

The present invention takes the aforementioned problems of the past into consideration, and an objective thereof is to realize a sterilizing apparatus having both excellent safety and operability.

Solution to Problem

In order to solve the aforementioned problems, a sterilizing apparatus according to an aspect of the present invention is a sterilizing apparatus that radiates light including ultraviolet rays onto a target object, characterized by emitting first wavelength light having a peak wavelength in a wavelength range of 190 nm or more and 230 nm or less, and second wavelength light having a peak wavelength in a wavelength range of 400 nm or more and 780 nm or less.

Advantageous Effects of Invention

According to an aspect of the present invention, an effect is demonstrated in that it is possible to provide a sterilizing apparatus having both excellent safety and operability.

DESCRIPTION OF EMBODIMENTS

Embodiment 1

Hereinafter, an embodiment of the present invention is as follows when described on the basis of FIGS. 1 to 3. A sterilizing apparatus according to the present embodiment radiates light including ultraviolet rays onto an affected area (target object) to sterilize the affected area. In the present specification, ultraviolet rays refer to light of a wavelength of 10 nm or more and less than 400 nm, and mean light of a wavelength range with which a sterilizing effect is generally recognized.

In the present embodiment, an explanation is given regarding an example of a configuration in which an ultraviolet laser is radiated as ultraviolet rays onto the affected area; however, it should be noted that the present invention is not restricted to the following configuration.

<Configuration of Sterilizing Apparatus 1>

Figure 1:
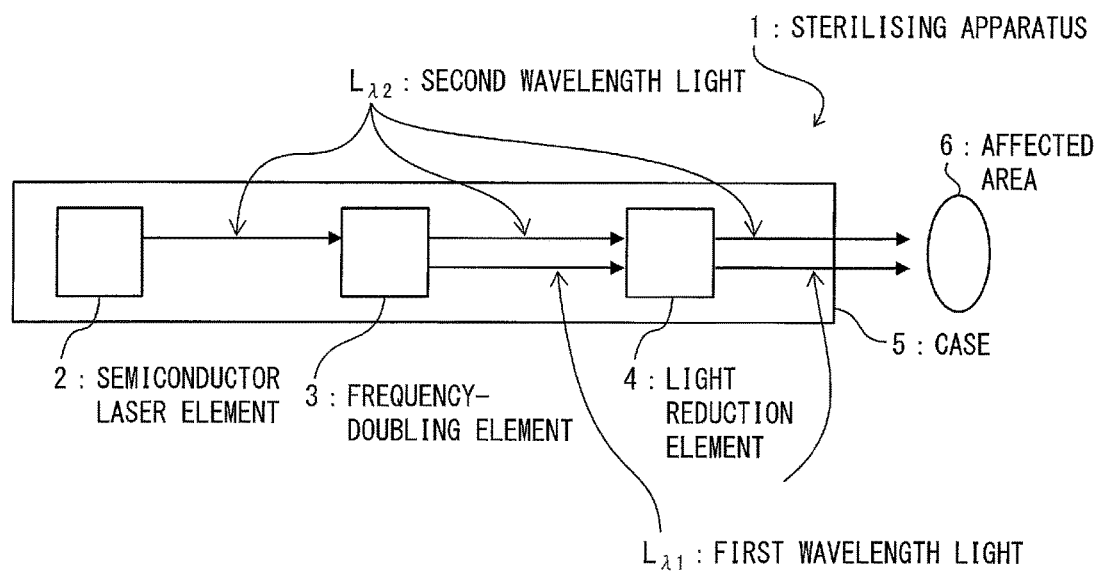
FIG. 1 is a block diagram depicting a configuration example of a sterilizing apparatus according to embodiment 1 of the present invention.

FIG. 1 is a block diagram depicting a configuration of a sterilizing apparatus 1 according to the present embodiment. As depicted in FIG. 1, the sterilizing apparatus 1 is provided with a semiconductor laser element (laser light source) 2, a frequency doubling element (frequency conversion element) 3, a light reduction element 4, and a case 5.

(Semiconductor Laser Element 2)

The semiconductor laser element 2 is a light source that oscillates (emits) second wavelength light $L_{\lambda 2}$ having a peak wavelength in a wavelength range of 400 nm or more and 460 nm or less. This second wavelength light $L_{\lambda 2}$ oscillated from the semiconductor laser element 2 is a coherent visible light laser in which the wavelength and the phase are uniform. The semiconductor laser element 2 emits the second wavelength light $L_{\lambda 2}$ toward the frequency-doubling element 3.

(Frequency-Doubling Element 3)

The frequency-doubling element 3 receives the second wavelength light $L_{\lambda 2}$ oscillated from the semiconductor laser element 2, doubles the frequency (halves the wavelength) of a portion of the second wavelength light $L_{\lambda 2}$, and performs conversion into first wavelength light $L_{\lambda 1}$ having a peak wavelength in a wavelength range of 200 nm or more and 230 nm or less ($\lambda_1 = \lambda_2/2$). Both of the first wavelength light $L_{\lambda 1}$, and the second wavelength light $L_{\lambda 2}$ are emitted at the same time as laser light from the frequency-doubling element 3.

This kind of frequency-doubling element 3 can be configured from a crystal non-linear optical material, for example. Beta-barium borate (BBC)), potassium fluoroboratoberyllate, lithium tetraborate, lithium rubidium tetraborate, magnesium barium fluoride, or the like may be cited as an example of a crystal non-linear optical material.

It should be noted that the details of the frequency-doubling element 3 are disclosed in Japanese Unexamined Patent Application Publication No. 2013-88822 and the like, and therefore, in the present specification, a detailed explanation of the frequency-doubling element 3 is omitted.

The frequency-doubling element 3 emits the first wavelength light $L_{\lambda 1}$ and the second wavelength light $L_{\lambda 2}$ toward the light reduction element 4.

(Light Reduction Element 4)

The light reduction element 4 is an element that reduces (attenuates) the second wavelength light $L_{\lambda 2}$ emitted from the frequency-doubling element 3. The light reduction element 4 reduces the second wavelength light $L_{\lambda 2}$ by absorbing or reflecting a portion of the second wavelength light $L_{\lambda 2}$. Meanwhile, the light reduction element 4 transmits, mostly without reducing, the first wavelength light $L_{\lambda 1}$ emitted from the frequency-doubling element 3.

An interference filter, a dichroic mirror, or the like may be cited as this kind of light reduction element 4. By changing the attenuation (reduction) rate, transmittance, reflectance, or the like of the light reduction element 4, control becomes possible such as freely changing the intensity ratio of the first wavelength light $L_{\lambda 1}$ and the second wavelength light $L_{\lambda 2}$. Furthermore, control becomes possible such as transmitting only light of a desired wavelength range from within the second wavelength light $L_{\lambda 2}$, and removing light of other wavelength ranges.

It should be noted that the light reduction element 4 may be omitted, and the second wavelength light $L_{\lambda 2}$ emitted from the frequency-doubling element 3 may be emitted from the sterilizing apparatus 1 without being reduced. In addition, the light of other wavelength ranges included in the second wavelength light $L_{\lambda2}$ (in other words, light outside of the wavelength range that is reduced by the light reduction element 4) may be reduced by freely adding an optical element having the same function as the light reduction element 4.

(Case 5)

The case 5 is a casing that accommodates the semiconductor laser element 2, the frequency-doubling element 3, and the light reduction element 4. The semiconductor laser element 2, the frequency-doubling element 3, and the light reduction element 4 are arranged in this order in a straight line within the case 5. The end section of the case 5 near the light reduction element 4 is open, and the first wavelength light $L_{\lambda1}$ and the second wavelength light $L_{\lambda2}$ are emitted from this end section to the outside.

<Action and Effect of the Sterilizing Apparatus 1>

Figure 2:
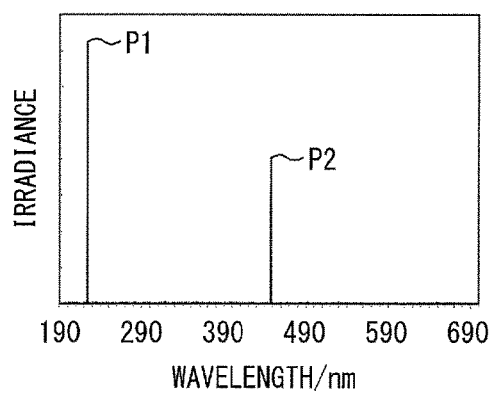
FIG. 2 is a graph depicting the spectrum of light that is radiated onto an affected area from the sterilizing apparatus depicted in FIG. 1.
Figure 3:
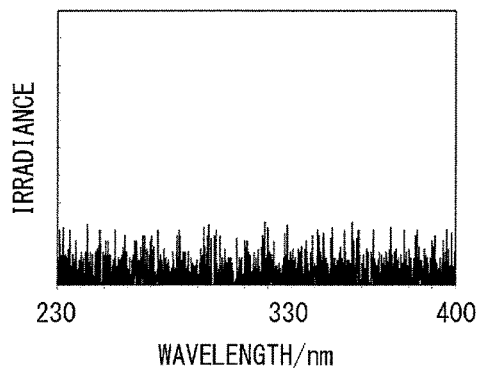
FIG. 3 is a graph in which the spectrum of a wavelength range of more than 230 and less than 400 nm depicted in FIG. 2 is enlarged.

FIG. 2 is a graph depicting the spectrum of light that is radiated onto an affected area 6 from the sterilizing apparatus 1, and FIG. 3 is a graph in which the spectrum of a wavelength range of more than 230 nm and less than 400 nm depicted in FIG. 2 is enlarged. In FIGS. 2 and 3, the vertical axes represent irradiance, and the horizontal axes represent wavelength.

As depicted in FIG. 2, the first wavelength light $L_{\lambda1}$ having a peak wavelength P1 in a wavelength range of 200 nm or more and 230 nm or less and the second wavelength light $L_{\lambda2}$ having a peak wavelength P2 in a wavelength range of 400 nm or more and 460 nm or less are radiated onto the affected area 6.

The first wavelength light $L_{\lambda1}$ having a peak wavelength P1 in a wavelength range of 200 nm or more and 230 nm or less is able to sterilize microbial bacteria without harming somatic cells. Therefore, the affected area 6 can be sterilized safely by radiating the first wavelength light $L_{\lambda1}$ onto the affected area 6.

Furthermore, the second wavelength light $L_{\lambda2}$ having a peak wavelength P2 in a wavelength range of 400 nm or more and 460 nm or less is visible to the human eye. Therefore, the irradiation range of the first wavelength light $L_{\lambda1}$ can be visualized by radiating the second wavelength light $L_{\lambda2}$ together with the first wavelength light $L_{\lambda1}$ onto the affected area 6.

In addition, as depicted in FIG. 3, it is understood that ultraviolet rays of a wavelength range of more than 230 nm and less than 400 nm are mostly not radiated onto the affected area 6, and constitute a noise level. In the case where the light intensity of the ultraviolet rays of a wavelength range of more than 230 nm and less than 400 nm radiated onto the affected area 6 is 3 mW/cm$^2$ or more, the possibility of harming somatic cells increases. Thus, in the sterilizing apparatus 1, harm to somatic cells is suppressed by having the light intensity of ultraviolet rays of a wavelength range of more than 230 nm and less than 400 nm radiated onto the affected area 6 be less than 3 mW/cm$^2$.

Furthermore, the sterilizing apparatus 1 provided with the frequency-doubling element 3 that converts a portion of the second wavelength light $L_{\lambda2}$ emitted from the semiconductor laser element 2 into the first wavelength light $L_{\lambda1}$ has the following advantages over conventional techniques.

Firstly, in the sterilizing apparatus 1, a portion of the second wavelength light $L_{\lambda2}$ is converted into the first wavelength light $L_{\lambda1}$ by the frequency-doubling element 3, and therefore there is hardly any occurrence of ultraviolet rays that are more than 230 nm and less than 400 nm with which there is a possibility of somatic cells being harmed. Therefore, it is not necessary to provide a spectral filter element or the like that prevents the inclusion of light outside of the wavelength range of 190 nm or more and 230 nm or less in the ultraviolet rays generated by an ultraviolet lamp, as in PTL 2, which is advantageous for space saving for the sterilizing apparatus 1. Furthermore, a spectral filter element does not have 100% transmittance, and also attenuates ultraviolet rays of the wavelength range of 190 nm or more and 230 nm or less, and therefore there is a decline in the usage efficiency of light. However, according to the sterilizing apparatus 1, this kind of decline in the usage efficiency of light does not occur, and it is therefore possible to realize a high usage efficiency of light.

Furthermore, PTL 2 discloses a technique with which argon for example is added to an excilamp, as another technique for preventing the inclusion of light outside of the wavelength range of 190 nm or more and 230 nm or less in ultraviolet rays; however, this technique involves an increase in manufacturing costs. However, according to the sterilizing apparatus 1, since the comparatively low-cost frequency-doubling element 3 is used, it is possible to suppress an increase in manufacturing costs.

Secondly, in the sterilizing apparatus 1, a portion of the second wavelength light $L_{\lambda2}$ emitted from the semiconductor laser element 2 passes through the frequency-doubling element 3 without being wavelength-converted, and is radiated onto the affected area 6 together with the first wavelength light $L_{\lambda1}$. Therefore, it becomes possible for the irradiation range of the first wavelength light $L_{\lambda1}$ to be visualized. Consequently, it is not necessary to provide both a light source that emits the first wavelength light $L_{\lambda1}$ for sterilization, and a light source that emits the second wavelength light $L_{\lambda2}$ for visualizing the irradiation range of the first wavelength light $L_{\lambda1}$, and therefore the sterilizing apparatus 1 can be reduced in size.

Thirdly, in the sterilizing apparatus 1, compared to the case where an ultraviolet lamp or an LED is used, it becomes possible for ultraviolet rays to be radiated onto the affected area 6 at a constant light intensity. In an actual surgical environment, it is required for ultraviolet rays having a target light intensity to be quickly radiated onto the affected area 6. However, in the case where ultraviolet rays from an ultraviolet lamp or an LED are condensed, when the distance between the affected area and the sterilizing apparatus changes, the irradiation area of the ultraviolet rays changes, and the light intensity density of the ultraviolet rays changes. However, according to the sterilizing apparatus 1, the first wavelength light $L_{\lambda1}$ and the second wavelength light $L_{\lambda2}$ are laser light and are both substantially parallel light. Therefore, even in the case where the distance between the affected area 6 and the sterilizing apparatus 1 changes, it is possible for the first wavelength light $L_{\lambda1}$ and the second wavelength light $L_{\lambda2}$ to be radiated onto the affected area 6 at a constant light intensity without the irradiation area changing.

Fourthly, in the sterilizing apparatus 1, since the first wavelength light $L_{\lambda1}$ is laser light, it becomes possible for the beam diameter of the first wavelength light $L_{\lambda1}$ to be reduced compared to the case where an ultraviolet lamp or an LED is used. Therefore, it becomes possible for the first wavelength light $L_{\lambda1}$ to be suitably radiated onto a complex, steep affected area 6.

Furthermore, as in the past, in a sterilization method in which ultraviolet rays are continuously radiated onto the affected area 6, the following problems can occur.

1. The light source generates heat.
2. There is a high possibility of there being a decline in the lifespan of the light source.

3. It is extremely dangerous for a physician.

4. Ultraviolet rays are obstructed from reaching a cut (referred to as a wound) made in surgery, by the hand or the like of the physician.

The aforementioned problems 1 and 2 are obvious to a person skilled in the art. Regarding the aforementioned problem 3, in a surgical environment, there is invariably a possibility of ultraviolet rays being reflected by a medical implement such as a scalpel. Therefore, in the case where ultraviolet rays include a wavelength that is harmful to the human body, it can be said to be a situation that is extremely dangerous for a physician.

Furthermore, regarding the aforementioned problem 4, during surgery, even if ultraviolet rays are continuously radiated, it is sufficiently feasible for the ultraviolet rays to be obstructed by a hand or the like of the physician. In this case, there is a decline in the intensity of the ultraviolet rays actually radiated onto the wound, and therefore a sufficient sterilizing effect by the continuous radiation of ultraviolet rays cannot be obtained.

Thus, the sterilizing apparatus 1 may intermittently emit the first wavelength light $L_{\lambda 1}$ and the second wavelength light $L_{\lambda 2}$ by controlling driving of the semiconductor laser element 2.

Since surgical site infections (SSIs) occur, it is conceivable that microbial bacteria reach the wound in all surgical environments. Upon reaching the wound, the microbial bacteria enter therein. During surgery, the physician frequently moves his or her hands and instruments, and therefore it is surmised that the time at which the microbial bacteria enter into the wound is approximately one minute after the start of the surgery. It is possible that the microbial bacteria may be sterilized by the ultraviolet rays prior to entering into the wound, but if the microbial bacteria enter deep into the wound, there is a decline in the sterilizing effect by the ultraviolet rays.

Furthermore, it is known that microbial bacteria form a biofilm as a self-defense reaction after reaching a wound. The time at which the biofilm is formed is approximately 30 minutes after reaching a wound. When this kind of phenomenon occurs, there is a considerable decline in the sterilizing effect by the ultraviolet rays.

For this reason, in order to effectively sterilize microbial bacteria, it can be said to be necessary to:

(1) radiate ultraviolet rays before microbial bacteria enter deep into a wound; and (2) radiate ultraviolet rays before microbial bacteria form a biofilm.

Consequently, in the case where the first wavelength light $L_{\lambda 1}$ is intermittently emitted from the sterilizing apparatus 1, it is preferable that the emitting/stopping of the first wavelength light $L_{\lambda 1}$ be switched at 10-minute intervals from the start of surgery, and it is more preferable that the emitting/stopping of the first wavelength light $L_{\lambda 1}$ be switched at one-minute intervals. It thereby becomes possible to save power for the sterilizing apparatus 1 while maintaining the sterilizing effect.

As mentioned above, the sterilizing apparatus 1 according to the present embodiment emits the first wavelength light $L_{\lambda 1}$ having a peak wavelength in a wavelength range of 200 nm or more and 230 nm or less and the second wavelength light $L_{\lambda 2}$ having a peak wavelength in a wavelength range of 400 nm or more and 460 nm or less.

The first wavelength light $L_{\lambda 1}$ having a peak wavelength in a wavelength range of 200 nm or more and 230 nm or less is able to sterilize microbial bacteria without harming somatic cells, and therefore the affected area 6 can be sterilized safely by radiating the first wavelength light $L_{\lambda 1}$ onto the affected area 6.

Furthermore, the second wavelength light $L_{\lambda 2}$ having a peak wavelength in a wavelength range of 400 nm or more and 460 nm or less is visible to the human eye, and therefore the irradiation range of the first wavelength light $L_{\lambda 1}$ can be visualized by radiating the second wavelength light $L_{\lambda 2}$ together with the first wavelength light $L_{\lambda 1}$ onto the affected area.

Consequently, according to the present embodiment, it is possible to realize the sterilizing apparatus 1 having both excellent safety and operability.

It should be noted that, in the present embodiment, an explanation has been given regarding a configuration in which light having a peak wavelength in a wavelength range of 200 nm or more and 230 nm or less is used as the first wavelength light $L_{\lambda 1}$, and light having a peak wavelength in a wavelength range of 400 nm or more and 460 nm or less is used as the second wavelength light $L_{\lambda 2}$.

However, the first wavelength light $L_{\lambda 1}$ may be light having a peak wavelength in a wavelength range of 190 nm or more and 230 nm or less, and the second wavelength light $L_{\lambda 2}$ may be light having a peak wavelength in a wavelength range of 400 nm or more and 780 nm or less. With a sterilizing apparatus that radiates the first wavelength light $L_{\lambda 1}$ and the second wavelength light $L_{\lambda 2}$ having peak wavelengths in the aforementioned wavelength ranges onto the affected area 6, it is possible for both excellent safety and operability to be achieved.

Modified Example 1

In the sterilizing apparatus according to the present invention, a first light source that emits the first wavelength light $L_{\lambda 1}$ having a peak wavelength in a wavelength range of 190 nm or more and 230 nm or less and a second light source that emits the second wavelength light $L_{\lambda 2}$ having a peak wavelength in a wavelength range of 400 nm or more and 780 nm or less may be provided instead of the semiconductor laser element 2 and the frequency-doubling element 3, respectively.

An ultraviolet ray-generating light source such as a semiconductor laser element, a lamp, or an LED capable of emitting the first wavelength light $L_{\lambda 1}$ may be cited as the first light source. An LED that emits the first wavelength light $L_{\lambda 1}$ is generally not commercially available; however, for example, it is possible to use the LED described in "Strategic Based Research Projects CREST Research Area 'Photonics and Quantum Optics for the Creation of Innovative Functions', Research Task 'Development of 230 to 350-nm Band InAlGaN-based High-efficiency Deep-UV Emitting Devices', Post-Completion Research Report p. 13". According to this LED, it is possible to emit ultraviolet rays having a peak wavelength of 222 nm. The light emission wavelength of this LED ranges from 220 nm to 250 nm; however, it is possible to realize an LED that emits the first wavelength light $L_{\lambda 1}$ if, for example, an LED having a shortened peak wavelength is used, and the current value is controlled in such a way that the light intensity at a wavelength of 230 nm to 250 nm becomes 3 mW/cm$^2$.

Furthermore, a visible light-generating light source such as a semiconductor laser element, a lamp, or an LED that is capable of emitting the second wavelength light $L_{\lambda 2}$ may be cited as the second light source. Generally, these light sources are commercially available, and therefore examples will not be given here.

It should be noted that, by using ultraviolet rays of 207 nm as the first wavelength light $L_{\lambda 1}$, it is possible to sterilize viruses appropriate for that wavelength such as adenoviruses, for example. In this way, by selecting a wavelength appropriate for viruses, it becomes possible to sterilize not only microbial bacteria but also viruses.

Modified Example 2

Furthermore, the sterilizing apparatus according to the present invention may be provided with a scanning mechanism that radiates the first wavelength light $L_{\lambda 1}$ onto the affected area 6 while scanning. It thereby becomes possible to radiate the first wavelength light $L_{\lambda 1}$ not only locally but also across a wide area. It is possible for the first wavelength light $L_{\lambda 1}$ to be radiated across a wide range even with an LED and an ultraviolet lamp; however, by radiating the first wavelength light $L_{\lambda 1}$, which is an ultraviolet laser, while scanning, it becomes possible to radiate the first wavelength light $L_{\lambda 1}$ at a constant light intensity even with respect to a complex, steep affected area 6.

Embodiment 2

Another embodiment of the present invention is as follows when described on the basis of FIG. 4. It should be noted that, for convenience of the explanation, members having the same functions as the members described in the aforementioned embodiment are denoted by the same reference signs, and descriptions thereof are omitted.

<Configuration of Sterilizing Apparatus 11>

Figure 4:
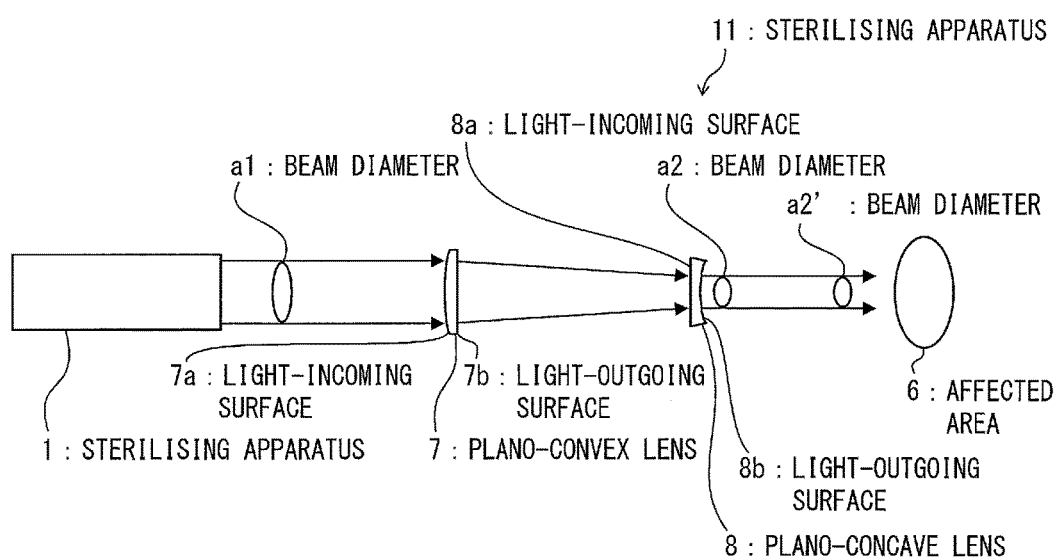
FIG. 4 is a block diagram depicting a configuration example of a sterilizing apparatus according to embodiment 2 of the present invention.

FIG. 4 is a block diagram depicting a configuration of a sterilizing apparatus 11 according to the present embodiment. It should be noted that reference sign a1 depicted in FIG. 4 indicates the beam diameter of the first wavelength light $L_{\lambda 1}$ emitted from the sterilizing apparatus 1, a2 indicates the beam diameter of the first wavelength light $L_{\lambda 1}$ emitted from a plano-concave lens 8, and a2' indicates the beam diameter of the first wavelength light $L_{\lambda 1}$ radiated onto the affected area 6.

As depicted in FIG. 4, the sterilizing apparatus 11 is provided with a plano-convex lens 7 and the plano-concave lens 8 in addition to the aforementioned sterilizing apparatus 1.

(Plano-Convex Lens 7)

The plano-convex lens 7 is an optical member that condenses the first wavelength light $L_{\lambda 1}$ and the second wavelength light $L_{\lambda 2}$ emitted from the sterilizing apparatus 1. The plano-convex lens 7 is provided with a light-incoming surface 7a having a convex curved surface shape upon which the first wavelength light $L_{\lambda 1}$ and the second wavelength light $L_{\lambda 2}$ emitted from the sterilizing apparatus 1 are made incident, and a light-outgoing surface 7b having a planar shape from which the first wavelength light $L_{\lambda 1}$ and the second wavelength light $L_{\lambda 2}$ are emitted.

The plano-convex lens 7 refracts the first wavelength light $L_{\lambda 1}$ and the second wavelength light $L_{\lambda 2}$ in such a way that the beam diameters of the first wavelength light $L_{\lambda 1}$ and the second wavelength light $L_{\lambda 2}$ become gradually smaller, and emits the first wavelength light $L_{\lambda 1}$ and the second wavelength light $L_{\lambda 2}$ toward the plano-concave lens 8.

(Plano-Concave Lens 8)

The plano-concave lens 8 is an optical member that converts the first wavelength light $L_{\lambda 1}$ and the second wavelength light $L_{\lambda 2}$ emitted from the plano-convex lens 7 into substantially parallel light. The plano-concave lens 8 is provided with a light-incoming surface 8a having a planar shape onto which the first wavelength light $L_{\lambda 1}$ and the second wavelength light $L_{\lambda 2}$ emitted from the plano-convex lens 7 are made incident, and a light-outgoing surface 8b having a concave curved surface shape from which the first wavelength light $L_{\lambda 1}$ and the second wavelength light $L_{\lambda 2}$ are emitted.

The plano-concave lens 8 refracts the first wavelength light $L_{\lambda 1}$ and the second wavelength light $L_{\lambda 2}$ in such a way that the first wavelength light $L_{\lambda 1}$ and the second wavelength light $L_{\lambda 2}$ both become substantially parallel light, and emits the first wavelength light $L_{\lambda 1}$ and the second wavelength light $L_{\lambda 2}$ toward the affected area 6.

<Action and Effect of the Sterilizing Apparatus 11>

The parallelism of light will be described with the first wavelength light $L_{\lambda 1}$ as an example. In the case where the parallelism of light is taken as k, the beam diameter of the first wavelength light $L_{\lambda 1}$ emitted from the plano-concave lens 8 is taken as a2, and the beam diameter of first wavelength light $L_{\lambda 1}$ radiated onto the affected area 6 is taken as a2', the parallelism k is represented by $$k = a2/a2' \qquad \text{expression (1)}.$$

In expression (1), in the case where completely parallel light is defined as k=1, if k>1, the first wavelength light $L_{\lambda 1}$ is condensed light (in other words, light having a beam diameter that decreases in the direction of advancement), and if k<1, the first wavelength light $L_{\lambda 1}$ is widened light (in other words, light having a beam diameter that increases in the direction of advancement). By using this parallelism k, it is possible to express the degree to which the light is close to being parallel.

Furthermore, in the case where the focal length of the plano-convex lens 7 is taken as f1, the absolute value of the focal length of the plano-concave lens 8 is taken as f2, and the spacing between the plano-convex lens 7 and the plano-concave lens 8 is taken as d, when $$d = f1 - f2 \qquad \text{expression (2)}$$

is satisfied, the first wavelength light $L_{\lambda 1}$ can be converted into completely parallel light.

It is possible to condense the first wavelength light $L_{\lambda 1}$ if the spacing d between the plano-convex lens 7 and the plano-concave lens 8 is smaller than the value (f1−f2) obtained from expression (2), and if larger, it is possible to widen the first wavelength light $L_{\lambda 1}$.

It should be noted that, in a surgical environment, it is feasible for the distance between the sterilizing apparatus 11 and the affected area 6 to realistically be 1 m or less. Therefore, during surgery, in the case where the first wavelength light $L_{\lambda 1}$ is radiated, the distance between the sterilizing apparatus 11 and the affected area 6 changes with an upper limit of 1 m.

Therefore, in the present specification, substantially parallel light means that $$0.2 < k < 5 \qquad \text{expression (3)}$$

is satisfied in expression (1).

In this way, by using the plano-convex lens 7 and the plano-concave lens 8, it is possible for first wavelength light $L_{\lambda 1}$ that is substantially parallel light having a beam diameter reduced from a1 to a2' to be radiated onto the affected area 6. Consequently, even in the case where the distance between the sterilizing apparatus 11 and the affected area 6 changes, it is possible for the first wavelength light $L_{\lambda 1}$ to be radiated onto the affected area 6 at a constant light intensity.

Furthermore, it becomes possible to reduce the beam diameter a2' of the first wavelength light $L_{\lambda 1}$ radiated onto the affected area 6; for example, the diameter a2' can be made to be less than 1 cm$^2$. Thus, it is possible for the first wavelength light $L_{\lambda 1}$ to be suitably radiated onto a complex, steep affected area 6.

It should be noted that, in the sterilizing apparatus 11, together with the first wavelength light $L_{\lambda 1}$, the second wavelength light $L_{\lambda 2}$ is also radiated onto the affected area 6 as substantially parallel light having a reduced beam diameter, and therefore the irradiation range of the first wavelength light $L_{\lambda 1}$ can be appropriately visualized.

In the present embodiment, an explanation has been given regarding a configuration in which the beam diameter a2' of the first wavelength light $L_{\lambda 1}$ radiated onto the affected area 6 is reduced (a1>a2') with respect to the beam diameter a1 of the first wavelength light $L_{\lambda 1}$ emitted from the sterilizing apparatus 1; however, the present invention is not restricted to this configuration. Using the same principle, a configuration may be implemented in which the beam diameter a2' of the first wavelength light $L_{\lambda 1}$ radiated onto the affected area 6 is increased (a1<a2') with respect to the beam diameter a1 of the first wavelength light $L_{\lambda 1}$ emitted from the sterilizing apparatus 1.

Embodiment 3

Another embodiment of the present invention is as follows when described on the basis of FIG. 5. It should be noted that, for convenience of the explanation, members having the same functions as the members described in the aforementioned embodiment are denoted by the same reference signs, and descriptions thereof are omitted.

<Configuration of Sterilizing Apparatus 12>

Figure 5:
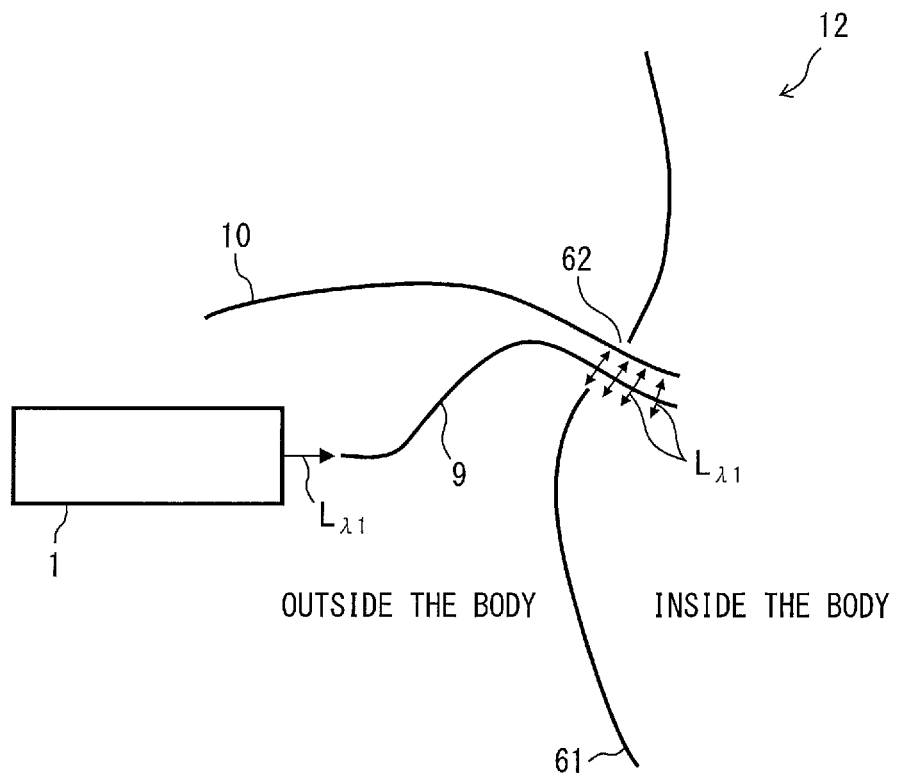
FIG. 5 is a block diagram depicting a configuration example of a sterilizing apparatus according to embodiment 3 of the present invention.

FIG. 5 is a block diagram depicting a configuration of a sterilizing apparatus 12 according to the present embodiment. This sterilizing apparatus 12 is used as a sterilizing apparatus for a medical implant. It should be noted that, although the second wavelength light is included in the light emitted from the sterilizing apparatus 1, in the drawing, the second wavelength light $L_{\lambda 2}$ is omitted and only the first wavelength light $L_{\lambda 1}$ is depicted.

As depicted in FIG. 5, the sterilizing apparatus 12 is provided with an optical fiber 9 in addition to the aforementioned sterilizing apparatus 1.

(Optical Fiber 9)

The optical fiber 9 is a light guide member that guides the first wavelength light $L_{\lambda 1}$ and the second wavelength light $L_{\lambda 2}$ emitted from the sterilizing apparatus 1. In this optical fiber 9, the first wavelength light $L_{\lambda 1}$ and the second wavelength light $L_{\lambda 2}$ are input from one end, and the first wavelength light $L_{\lambda 1}$ and the second wavelength light $L_{\lambda 2}$ are emitted from a plurality of light-outgoing holes formed in the peripheral surface near the other end.

The optical fiber 9 has a two-layer structure in which a central core is covered by cladding having a lower refractive index than the core. Quartz glass (silicon oxide) having hardly no laser light absorption loss is used as the main component of the core, and quartz glass or a synthetic resin material having a lower refractive index than the core is used as the main component of the cladding.

<Action and Effect of the Sterilizing Apparatus 12>

Left ventricular assist pumps and catheters 10 are widely known as medical implants. The importance of left ventricular assist pumps is increasing in cardiac treatment. These have become the hope of patients waiting for a complete cardiac transplant. However, there is a definitive problem with medical implants; infections can easily occur during showers or the like from a portion where the medical implant comes into contact with outside of the body, in other words, with the left ventricular assist pump, the electrical transmission path to the power source, and with the catheter 10, the outlet portion (where a pump or the like is often placed) of the catheter placed outside of the body.

According to the sterilizing apparatus 12, it is possible to radiate the first wavelength light $L_{\lambda 1}$ and sterilize microbial bacteria and viruses that are present near the catheter 10, also while the catheter 10 is inside of the body. Naturally, there is no harm to the somatic cells near the catheter 10 due to the first wavelength light $L_{\lambda 1}$.

The first wavelength light $L_{\lambda 1}$ and the second wavelength light $L_{\lambda 2}$ emitted from the sterilizing apparatus 1 enter the optical fiber 9. The catheter 10 is inserted through skin 61 into the human body through a perforation 62 that has been opened in the skin 61.

The first wavelength light $L_{\lambda 1}$ propagates through the optical fiber 9, and is emitted from the peripheral surface of the optical fiber 9, near the catheter 10. It is thereby possible to radiate the first wavelength light $L_{\lambda 1}$ onto the catheter 10, and reduce the probability of infection caused by the catheter 10, also while the catheter 10 is inside of the body.

It should be noted that the first wavelength light $L_{\lambda 1}$ and the second wavelength light $L_{\lambda 2}$ emitted from the sterilizing apparatus 1 are laser light and can therefore be made incident upon the optical fiber 9 with a high coupling efficiency. Therefore, according to the sterilizing apparatus 12, the usage efficiency of light can be improved.

Embodiment 4

Another embodiment of the present invention is as follows when described on the basis of FIGS. 6 to 10. It should be noted that, for convenience of the explanation, members having the same functions as the members described in the aforementioned embodiment are denoted by the same reference signs, and descriptions thereof are omitted.

In the present embodiment, an explanation will be given regarding specific application examples of the sterilizing apparatus according to the present invention.

Application Example 1

Figure 6:
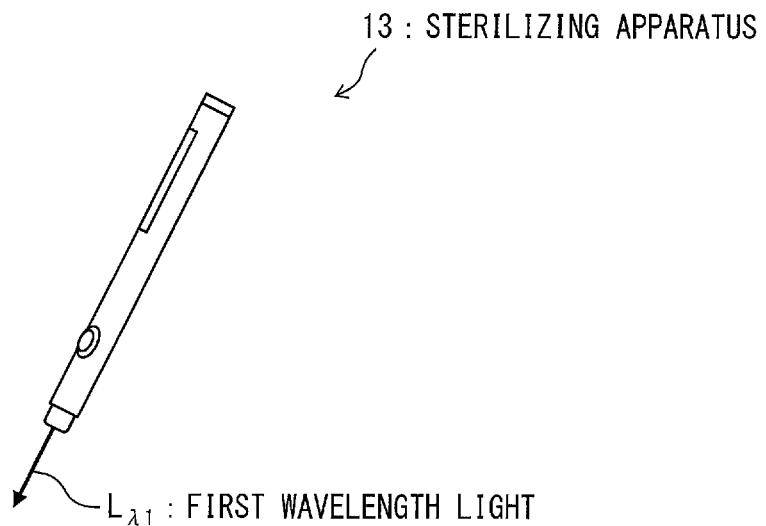
FIG. 6 is a schematic diagram depicting an application example of the present invention.

FIG. 6 is a perspective view depicting a pencil-type sterilizing apparatus 13. As depicted in FIG. 13, it is feasible for the sterilizing apparatus according to the present invention to be implemented as the pencil-type sterilizing apparatus 13. Furthermore, the optical fiber 9 may be connected to the pencil-type sterilizing apparatus 13 for the first wavelength light $L_{\lambda 1}$ and the second wavelength light $L_{\lambda 2}$ (not depicted) to be propagated and emitted.

For example, implementing a sterilizing apparatus in which the frequency-doubling element 3 is used, as the pencil-type sterilizing apparatus 13 makes battery driving possible. Therefore, the pencil-type sterilizing apparatus 13 can be conveniently used in an actual surgical environment.

Application Example 2

Figure 7:
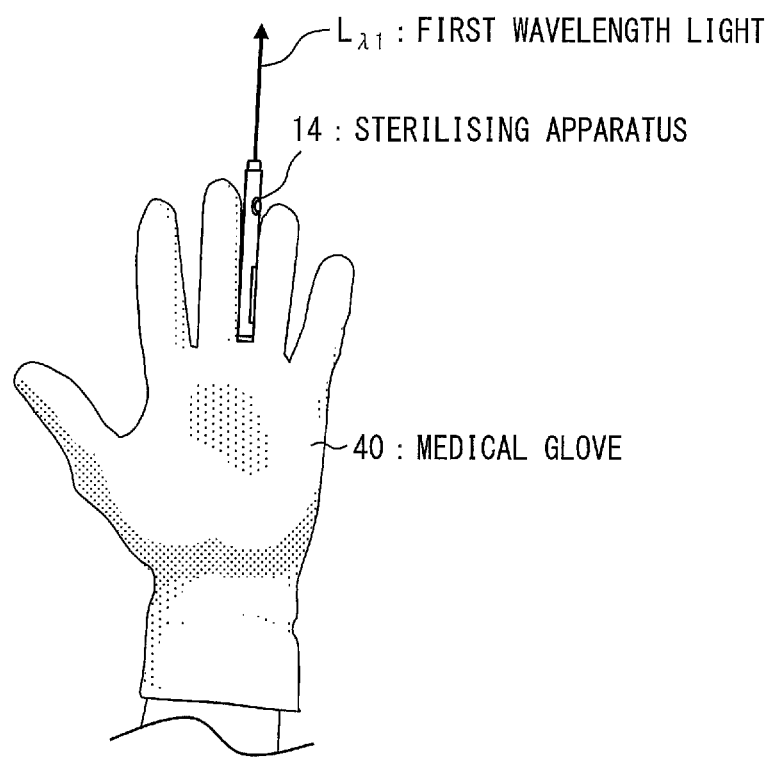
FIG. 7 is a schematic diagram depicting an application example of the present invention.

FIG. 7 is a schematic view depicting a sterilizing apparatus 14 that can be attached to a medical glove 40. As depicted in FIG. 7, the sterilizing apparatus 14 may be attached to the medical glove 40. It thereby becomes possible for the first wavelength light $L_{\lambda 1}$ and the second wavelength light $L_{\lambda 2}$ (not depicted) to be quickly radiated onto a location at which an operator has pointed.

Application Example 3

Figure 8:
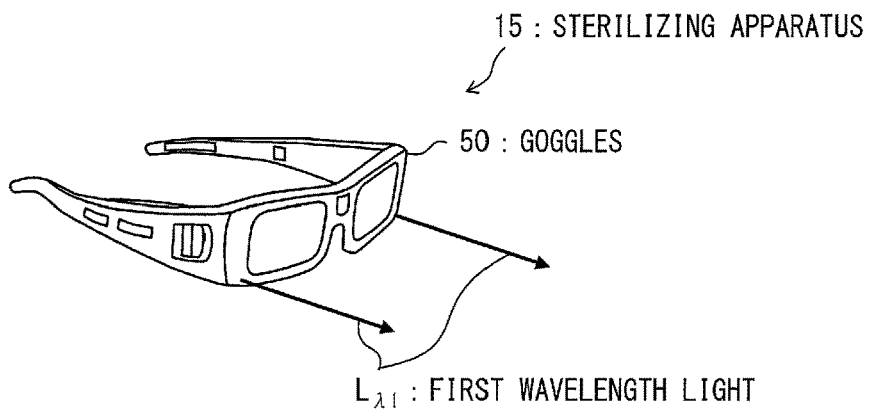
FIG. 8 is a schematic diagram depicting an application example of the present invention.

FIG. 8 is a schematic view depicting a medical goggle-type sterilizing apparatus 15. For this medical goggle-type sterilizing apparatus 15, the sterilizing apparatus 1, which is not depicted, is housed in goggles 50.

It is desirable that the goggles 50 having the sterilizing apparatus 1 housed therein be provided with the function of cutting out ultraviolet rays as well as the functions of commonly used medical goggles. Furthermore, by attaching a camera, a sensor, or the like to the goggles 50, it becomes possible to radiate the first wavelength light $L_{\lambda 1}$ and the second wavelength light $L_{\lambda 2}$ (not depicted) in the line of sight of the operator.

Application Example 4

Figure 9:
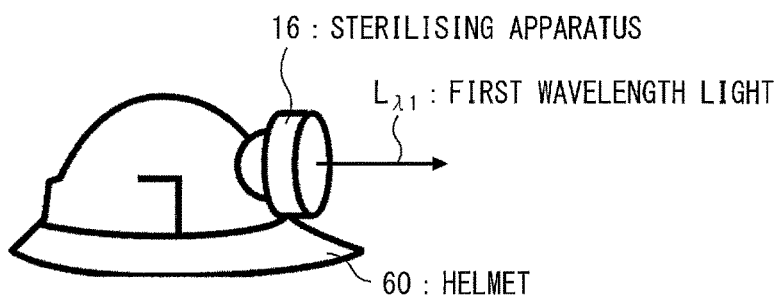
FIG. 9 is a schematic diagram depicting an application example of the present invention.

FIG. 9 is a schematic view depicting a sterilizing apparatus 16 that can be attached to a helmet 60. As depicted in FIG. 9, the sterilizing apparatus 16 may be attached to the helmet 60. Furthermore, by attaching, for example, a camera, a sensor, or the like to the helmet 60, it becomes possible to radiate the first wavelength light $L_{\lambda 1}$ and the second wavelength light $L_{\lambda 2}$ (not depicted) in the line of sight of the operator.

Application Example 5

Figure 10:
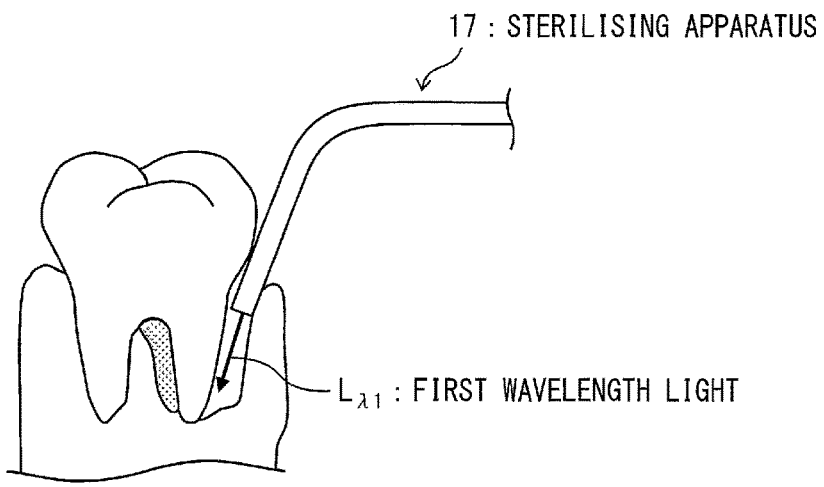
FIG. 10 is a schematic diagram depicting an application example of the present invention.

FIG. 10 is a schematic view depicting a sterilizing apparatus 17 that can be used in dental surgery. In dental surgery, it is known that periodontal disease in particular recurs quickly. In the mouth, both good bacteria and bad bacteria are present, and both bacteria generate a biofilm. Microbial bacteria take refuge in and multiply in that biofilm.

In periodontal disease, in addition to a deep groove called a periodontal pocket being formed and it not being possible for a drug to be physically administered, it is not possible for the microbial bacteria in the biofilm to be sterilized by the drug.

However, as depicted in FIG. 10, it is possible for the periodontal pocket to be sterilized by means of ultraviolet rays according to the sterilizing apparatus 17, and it becomes possible to treat periodontal disease by radiating the first wavelength light $L_{\lambda 1}$ onto a local site by means of the sterilizing apparatus 17.

It should be noted that the application examples of the sterilizing apparatus according to the present invention are not restricted to the aforementioned. For example, a sterilizing apparatus may be applied to an endoscope. In this case, a sterilizing apparatus is housed inside an endoscope, and the first wavelength light $L_{\lambda 1}$ and the second wavelength light $L_{\lambda 2}$ emitted by the sterilizing apparatus are propagated by means of an optical fiber and emitted from the tip end of the endoscope. It thereby becomes possible to locally radiate the first wavelength light $L_{\lambda 1}$ and the second wavelength light $L_{\lambda 2}$ while looking at an endoscope camera image.

SUMMARY

A sterilizing apparatus according to aspect 1 of the present invention is a sterilizing apparatus that radiates light including ultraviolet rays onto a target object (affected area 6), characterized by emitting first wavelength light having a peak wavelength in a wavelength range of 190 nm or more and 230 nm or less, and second wavelength light having a peak wavelength in a wavelength range of 400 nm or more and 780 nm or less.

In the aforementioned configuration, the sterilizing apparatus emits first wavelength light having a peak wavelength in a wavelength range of 190 nm or more and 230 nm or less. The first wavelength light having a peak wavelength in a wavelength range of 190 nm or more and 230 nm or less is able to sterilize microbial bacteria without harming somatic cells. Therefore, the target object can be sterilized safely by radiating the first wavelength light onto the target object.

Furthermore, in the aforementioned configuration, the sterilizing apparatus emits second wavelength light having a peak wavelength in a wavelength range of 400 nm or more and 780 nm or less. The second wavelength light having a peak wavelength in a wavelength range of 400 nm or more and 780 nm or less is visible to the human eye. Therefore, the irradiation range of the first wavelength light can be visualized by radiating the second wavelength light together with the first wavelength light onto the target object.

Consequently, according to the aforementioned configuration, it is possible to realize a sterilizing apparatus having both excellent safety and operability.

Furthermore, for a sterilizing apparatus according to aspect 2 of the present invention, in the aforementioned aspect 1, the intensity of light of a wavelength range of more than 230 nm and less than 400 nm radiated onto the target object may be less than 3 mW/cm$^2$.

In the case where the intensity of light of a wavelength range of more than 230 nm and less than 400 nm radiated onto the target object is 3 mW/cm$^2$ or more, the possibility of harming somatic cells increases. Thus, by making the intensity of light of a wavelength range of more than 230 nm and less than 400 nm radiated onto the target object be less than 3 mW/cm$^2$, it becomes possible to suppress harm to somatic cells.

Consequently, according to the aforementioned configuration, the safety of the sterilizing apparatus can be further improved.

Furthermore, for a sterilizing apparatus according to aspect 3 of the present invention, in the aforementioned aspect 1 or 2, there may be provided: a laser light source that oscillates the second wavelength light; and a frequency conversion element that receives the second wavelength light oscillated from the laser light source, and converts a portion of the second wavelength light into the first wavelength light, and the frequency conversion element may emit the first wavelength light and the second wavelength light that has not been converted into the first wavelength light.

In the aforementioned configuration, the sterilizing apparatus is provided with a frequency conversion element that converts a portion of the second wavelength light emitted from the laser light source into the first wavelength light, and the first wavelength light and the second wavelength light emitted from this frequency conversion element are radiated onto the target object. According to this kind of configuration, there are the following advantages over conventional techniques.

Firstly, in the aforementioned configuration, a portion of the second wavelength light is converted into the first wavelength light by the frequency conversion element, and therefore there is no occurrence of ultraviolet rays that are more than 230 nm and less than 400 nm with which there is a possibility of somatic cells being harmed. Therefore, it is not necessary to provide a spectral filter element or the like that prevents the inclusion of light outside of the wavelength range of 190 nm or more and 230 nm or less in the ultraviolet rays generated by an ultraviolet lamp, as in PTL 2, which is advantageous for space saving for the sterilizing apparatus. Furthermore, a spectral filter element does not have 100% transmittance, and also attenuates ultraviolet rays of the wavelength range of 190 nm or more and 230 nm or less, and therefore there is a decline in the usage efficiency of light. However, according to the aforementioned configuration, this kind of decline in the usage efficiency of light does not occur, and it is therefore possible to realize a high usage efficiency of light.

Furthermore, PTL 2 discloses a technique with which argon for example is added to an excilamp, as another technique for preventing the inclusion of light outside of the wavelength range of 190 nm or more and 230 nm or less in ultraviolet rays; however, this technique involves an increase in manufacturing costs. However, according to the aforementioned configuration, since a comparatively low-cost frequency conversion element is used, it is possible to suppress an increase in manufacturing costs.

Secondly, in the aforementioned configuration, a portion of the second wavelength light emitted from the laser light source passes through the frequency conversion element without being wavelength-converted, and is radiated onto the target object together with the first wavelength light. Therefore, it is possible for the irradiation range of the first wavelength light to be visualized. Consequently, it is not necessary to provide both a light source that emits the first wavelength light for sterilization, and a light source that emits the second wavelength light for visualizing the first wavelength light, and therefore the sterilizing apparatus can be reduced in size.

Thirdly, in the aforementioned configuration, compared to a configuration in which an ultraviolet lamp or an LED is used, it becomes possible for the first wavelength light to be radiated onto the target object at a constant light intensity. In an actual surgical environment, it is required for ultraviolet rays having a target intensity to be quickly radiated onto an affected area (target object). However, in the case where ultraviolet rays from an ultraviolet lamp or an LED are condensed, when the distance between the sterilizing apparatus and the affected area changes, the irradiation area of the light changes, and the light intensity density of the ultraviolet rays changes. However, according to the aforementioned configuration, the first wavelength light and the second wavelength light are laser light and both become substantially parallel light. Therefore, even in the case where the distance between the sterilizing apparatus and the target object changes, it is possible for the first wavelength light and the second wavelength light to be radiated onto the target object at a constant light intensity without the irradiation area changing.

Fourthly, in the aforementioned configuration, since the first wavelength light is laser light, it becomes possible for the beam diameter of the first wavelength light to be reduced compared to the case where an ultraviolet lamp or an LED is used. Therefore, it becomes possible for the first wavelength light to be suitably radiated onto a complex, steep affected area (target object).

Furthermore, for a sterilizing apparatus according to aspect 4 of the present invention, in any of the aforementioned aspects 1 to 3, there may be provided a light reduction element that reduces the second wavelength light.

According to the aforementioned configuration, by changing the attenuation rate, transmittance, reflectance, or the like of the light reduction element, control becomes possible such as freely changing the intensity ratio of the first wavelength light and the second wavelength light radiated onto the target object. Furthermore, according to the aforementioned configuration, control becomes possible such as transmitting only light of a desired wavelength range from within the second wavelength light, and removing light of other wavelength ranges by means of the light reduction element.

Furthermore, for a sterilizing apparatus according to aspect 5 of the present invention, in any of the aforementioned aspects 1 to 4, the first wavelength light may be substantially parallel light, and the second wavelength light may be substantially parallel light.

In the aforementioned configuration, because the first wavelength light and the second wavelength light are both substantially parallel light, the irradiation area does not change even in the case where the distance between the sterilizing apparatus and the target object has changed.

Consequently, according to the aforementioned configuration, it is possible for the first wavelength light and the second wavelength light to be radiated onto the target object at a constant light intensity even in the case where the distance between the sterilizing apparatus and the target object has changed, and therefore the operability of the sterilizing apparatus can be improved.

Furthermore, for a sterilizing apparatus according to aspect 6 of the present invention, in any of the aforementioned aspects 1 to 5, the beam diameter of the first wavelength light radiated onto the target object may be less than 1 $cm^2$.

According to the aforementioned configuration, because the beam diameter of the first wavelength light radiated onto the target object is less than 1 $cm^2$, it is possible for the first wavelength light to be suitably radiated onto a complex, steep affected area (target object).

Furthermore, for a sterilizing apparatus according to aspect 7 of the present invention, in any of the aforementioned aspects 1 to 6, the first wavelength light may be emitted intermittently.

According to the aforementioned configuration, because the first wavelength light is radiated intermittently onto the target object, it is possible to prolong the lifespan of the light source, save power for the sterilizing apparatus, and the like while maintaining the sterilizing effect.

The present invention is not restricted to the aforementioned embodiments, various alterations are possible within the scope indicated in the claims, and embodiments obtained by appropriately combining the technical means disclosed in each of the different embodiments are also included within the technical scope of the present invention. In addition, novel technical features can be formed by combining the technical means disclosed in each of the embodiments.

[Supplement]

The present invention can also be expressed as follows. More specifically, the sterilizing apparatus according to the present invention is a sterilizing apparatus that generates at least one ultraviolet ray, characterized by being provided with a light source having a peak in a first wavelength that is a wavelength of approximately 190 nm to 230 nm, and also having a peak in a second wavelength that is a wavelength of approximately 400 nm to 780 nm.

Furthermore, in the sterilizing apparatus according to the present invention, it is preferable that the light intensity density of a third wavelength that is a wavelength of approximately 230 nm to 400 nm be less than 3 $mW/cm^2$.

Furthermore, in the sterilizing apparatus according to the present invention, it is preferable that a device that attenuates light of the second wavelength be provided.

Furthermore, in the sterilizing apparatus according to the present invention, it is preferable that light of the first wavelength and the second wavelength be substantially parallel light.

Furthermore, in the sterilizing apparatus according to the present invention, it is preferable that the beam diameter of the first wavelength be less than 1 cm².

Furthermore, in the sterilizing apparatus according to the present invention, it is preferable that light of the first wavelength be generated in a pulsed manner.

INDUSTRIAL APPLICABILITY

The present invention can be used for a sterilizing apparatus that radiates ultraviolet rays, and, in particular, can be preferably used for a medical instrument that is used during surgery.

REFERENCE SIGNS LIST

1 Sterilizing apparatus
2 Semiconductor laser element (light source)
3 Frequency-doubling element (frequency conversion element)
4 Light reduction element
5 Case
6 Affected part (target object)
7 Plano-convex lens
8 Plano-concave lens
9 Optical fiber
10 Catheter
11 Sterilizing apparatus
12 Sterilizing apparatus
13 Sterilizing apparatus
14 Sterilizing apparatus
15 Sterilizing apparatus
16 Sterilizing apparatus
17 Sterilizing apparatus
61 Skin
62 Perforation (target object)
a2' Beam diameter
$L_{\lambda 1}$ First wavelength light
$L_{\lambda 2}$ Second wavelength light
P1 Peak wavelength
P2 Peak wavelength

The invention claimed is:

1. A sterilizing apparatus radiating light including ultraviolet rays onto a target object, comprising:
   a laser light source oscillating second wavelength light having a peak wavelength in a range of 400 nm or more and 460 nm or less;
   a light frequency converter receiving the second wavelength light oscillated from the laser light source, the light frequency converter converting a portion of the second wavelength light into first wavelength light having a peak wavelength in a range of 190 nm or more and 230 nm or less,
   the light frequency converter emitting the first wavelength light and the second wavelength light not being converted into the first wavelength light; and
   a light intensity reducer changing the ratio of the light intensity of the first wavelength light to the light intensity of the second wavelength light while the sterilizing apparatus is operated, wherein
   light intensity of the ultraviolet rays of a wavelength range of more than 230 nm and less than 400 nm radiated onto the target object is less than 3 mW/cm²,
   the ultraviolet rays of the wavelength range of more than 230 nm and less than 400 nm radiated onto the target object with less than 3 mW/cm² of the light intensity suppresses harm to somatic cells, and
   the light intensity reducer reduces the second wavelength light by absorbing or reflecting a portion of the second wavelength light emitted from the light frequency converter, and, the light intensity reducer transmits, without reducing, the first wavelength light emitted from the light frequency converter.

2. The sterilizing apparatus according to claim 1, wherein the light intensity reducer changes the ratio of the light intensity of the first wavelength light to the light intensity of the second wavelength light while maintaining the light intensity of the ultraviolet rays of the wavelength range of more than 230 nm and less than 400 nm to be less than 3 mW/cm².

3. The sterilizing apparatus according to claim 1, wherein the light frequency converter being a light frequency doubling converter,
and being provided with the light intensity reducer that reduces the second wavelength light.

4. The sterilizing apparatus according to claim 1, wherein the light intensity reducer receives the first wavelength light and the second wavelength light emitted from the light frequency converter and the light intensity reducer emits the first wavelength light and the second wavelength light to outside of the sterilizing apparatus.

5. The sterilizing apparatus according to claim 4, wherein the first wavelength light and the second wavelength light emitted from the light intensity reducer to outside of the sterilizing apparatus are both substantially parallel light.

* * * * *